United States Patent [19]

Boozalis et al.

[11] 4,119,674
[45] Oct. 10, 1978

[54] PROCESS FOR PRODUCTION OF 1,1,1-TRICHLOROETHANE AND VINYLIDENE CHLORIDE

[75] Inventors: Theodore S. Boozalis; John B. Ivy, both of Lake Jackson, Tex.

[73] Assignee: The Dow Chemical Company, Midland, Mich.

[21] Appl. No.: 718,642

[22] Filed: Aug. 30, 1976

[51] Int. Cl.$^2$ .................... C07C 21/18; C07C 17/00; C07C 21/00

[52] U.S. Cl. ........................... 260/658 R; 260/652 P; 260/654 S; 260/656 R; 260/660

[58] Field of Search .................... 260/652 P, 652.5 P, 260/654 R, 654 P, 654 H, 654 S, 660, 662 R, 658 R, 656 R

[56] References Cited

U.S. PATENT DOCUMENTS

| 2,748,176 | 5/1956 | Morris | 260/652 P |
| 2,952,713 | 9/1960 | Pallenberg | 260/652 P |
| 3,548,014 | 12/1970 | Jacobowsky | 260/652 P |
| 3,876,714 | 4/1975 | Coppens | 260/656 R |
| 3,920,761 | 11/1975 | Krome | 260/656 R |
| 3,935,286 | 1/1976 | Strini et al. | 260/652 P |
| 4,060,460 | 11/1977 | Smalley et al. | 260/652 P |

FOREIGN PATENT DOCUMENTS

| 609,223 | 11/1960 | Canada | 260/652 P |
| 670,594 | 9/1963 | Canada | 260/652 P |

Primary Examiner—O. R. Vertiz
Assistant Examiner—Gary P. Straub
Attorney, Agent, or Firm—G. R. Baker

[57] ABSTRACT

An improved process for preparation of 1,1,1-trichloroethane and/or vinylidene chloride by the direct high temperature chlorination of ethane, ethyl chloride, ethylene, 1,1-dichloroethane or mixtures thereof wherein the relatively small quantities of unsaturated, chlorinated compounds containing more than two carbon atoms formed as by-products are selectively reacted with elemental chlorine to produce stable compounds which are not detrimental to the efficient operation of subsequent iron catalyzed hydrochlorination and dehydrochlorination steps. This is accomplished in the presence of relatively high concentration of valuable unsaturated $C_2$'s.

2 Claims, No Drawings

PROCESS FOR PRODUCTION OF 1,1,1-TRICHLOROETHANE AND VINYLIDENE CHLORIDE

BACKGROUND OF THE INVENTION

When ethane, ethyl chloride, ethylene, 1,1-dichloroethane or a mixture of these compounds is reacted with chlorine at elevated temperatures there is produced 1,1,1-trichloroethane and vinylidene chloride, very desirable products. Also formed, however, are numerous by-products. It is common practice to conduct all or part of the high temperature chlorination reactor effluent to a liquid phase hydrochlorination reactor employing ferric chloride as catalyst, where unsaturated $C_2$ by-products are combined with hydrogen chloride (also a by-product of the direct chlorination) to form saturated chlorinated hydrocarbons that can be recycled to the high temperature chlorination reactor to yield more of the desired products. For example, vinyl chloride is converted to 1,1-dichloroethane and ethylene to ethyl chloride in the hydrochlorinator. If increased yield of 1,1,1-trichloroethane is desired, vinylidene chloride can be passed through the hydrochlorination reactor where it is also combined with HCl to form 1,1,1-trichloroethane. Conversely, if vinylidene chloride is the desired product of the process, dehydrochlorination of 1,1,1-trichloroethane can be readily accomplished in an iron catalyzed, liquid phase reaction.

The major detrimental by-products of the high temperature chlorination with respect to further processing of the chlorinator effluent are unsaturated, chlorinated compounds containing more than two carbon atoms and although formed in relatively small quantities by various polymerization reactions which occur at these conditions, these products create problems. The ferric iron catalyst used in the hydrochlorination and/or dehydrochlorination steps of the process interacts with and is deactivated by small amounts of chlorinated, unsaturated by-products containing more than two carbon atoms such as those appearing in the reactor effluent. Thus, if these compounds are allowed to remain in the reactor effluent the efficiencies of the catalyzed hydrochlorination and dehydrochlorination steps of subsequent processing are greatly reduced. Because of their boiling points and concentration ranges relative to the various $C_2$'s present in the effluent from a high temperature chlorination reactor, removal of the unsaturated polymerization products by distillation is very difficult. Also, removal of these compounds by any technique, e.g., distillation which involves their concentration is further complicated by their instability. Some of these compounds polymerize rapidly when concentrated, to form rubber-like polymers which plug process equipment.

It is well known that under the proper reaction conditions unsaturated hydrocarbons and chlorohydrocarbons can be readily and selectively reacted with elemental chlorine in the presence of much greater relative concentrations of saturated chlorinated hydrocarbons. However, the thermal chlorination reactor effluent even after quenching and flashing to remove the lower boiling compounds still contains valuable unsaturated $C_2$'s in many times the concentration of the undesirable by-products which are to be chlorinated. Also, upon reaction with chlorine the unsaturated $C_2$'s form compounds of little or no commercial value, e.g., vinylidene chloride chlorinates to yield tetrachloroethanes.

Therefore, it would be advantageous to provide a process for the deactivation of these unsaturated, chlorinated by-products containing more than 2 carbon atom compounds in the effluent of a thermal chlorinator before further processing the effluent stream.

This object as well as others will become apparent to those skilled in the art to which the invention pertains from the following description and claims.

BRIEF DESCRIPTION OF THE INVENTION

In the present improved process the effluent from a high temperature chlorination reactor, in which chlorine is contacted with ethane, ethyl chloride, ethylene, 1,1-dichloroethane or mixtures thereof at temperatures from 400° C. to 500° C., is quenched to less than about 100° C. and prior to any further processing, i.e., hydrochlorination and/or dehydrochlorination, the effluent is subjected to a low temperature, selective reaction with elemental chlorine thereby rendering the various unsaturated chlorinated impurities containing more than 2 carbon atoms, which result from polymerization reactions, harmless to the efficient operation of hydrochlorination and/or dehydrochlorination reactions.

DETAILED DESCRIPTION OF THE INVENTION

As stated above the effluent from a high temperature chlorination reactor in which chlorine is reacted with ethane, ethyl chloride, ethylene, 1,1-dichloroethane or mixtures thereof at temperatures of 400° C. to 500° C. is customarily subjected, subsequent to cooling to less than about 100° C., to liquid phase, iron catalyzed hydrochlorination and/or dehydrochlorination. In accordance with the present invention the portion of the high temperature chlorination reactor effluent intended to be hydrochlorinated and/or dehydrochlorinated is chlorinated at temperatures of 0°–100° C., but preferably at a temperature within the range of from about 10° C. to about 50° C. The low temperature chlorination is carried out in the liquid phase and in the absence of catalyst.

Pressure employed for the low temperature chlorination preferably is slightly above atmospheric. Operable pressure is within the range of about 14 to about 100 psig (0.9 to 6.8 atmospheres).

With respect to the chlorine employed, an amount approximately stoichiometric based on the unsaturated polymerization products present is preferred. Less than about stoichiometric amounts, although still operable, merely lessen the efficiency of the process.

The following example demonstrates that these undesirable compounds can be selectively reacted with chlorine in the presence of much greater concentration of valuable unsaturated $C_2$'s and thereby rendered harmless to the efficient operation of the process.

Example I

A mixture consisting of compounds present in a typical high temperature chlorinator effluent, after quenching to about 30° C. and allowing the majority of gaseous components at this temperature to flash away from the liquid phase, is represented in Table I. A 1000 cc sample of this liquid was placed in a round-bottom, stirred, glass flask. Gaseous chlorine was metered into this liquid through a glass frit. The reaction mixture was sampled periodically for analysis. Table I shows the composition of the reaction mixture after about 0.3 mole percent and after about 0.6 mole percent chlorine had been added. As can be seen, the chlorinated unsaturated polymerization products were reacted quantitatively with little or no detectable loss of valuable chlorinated, unsaturated C$_2$'s. Table I is normalized to 100% based on the components listed. Heavy polychlorinated compounds produced by the chlorination of the unsaturated polymerization products are not shown on the table.

Table I

| Mole % Cl$_2$ Added | Mole Percent | | |
|---|---|---|---|
| | 0 | 0.3 | 0.6 |
| Vinyl Chloride | 2.10 | 2.14 | 2.05 |
| Chlorobutene | trace | — | — |
| trans-1,2-Dichloroethylene | 2.41 | 2.42 | 2.33 |
| Chloroprene | 0.40 | 0.20 | — |
| 1,1-Dichloroethane | 0.03 | 0.03 | 0.04 |
| 1-Chloro-1,3-Butadiene | 0.07 | — | — |
| Carbon Tetrachloride | 0.04 | 0.04 | 0.03 |
| cis-1,2-Dichloroethylene | 4.56 | 4.48 | 4.66 |
| Chloroform | 0.11 | 0.11 | 0.13 |
| Trichloroethylene | 3.65 | 3.57 | 3.71 |
| Ethylene Dichloride | 75.30 | 75.40 | 75.60 |
| Perchloroethylene | 0.78 | 0.78 | 0.82 |
| Vinylidene Chloride | 10.60 | 10.80 | 10.60 |

What is claimed is:

1. In a process for chlorinating a member of the group consisting of ethane, ethylene, ethyl chloride, 1,1-dichloroethane, and mixtures thereof by the thermal chlorination to produce one or more of 1,1,1-trichloroethane, 1,1-dichloroethane, 1,1-dichloroethylene, as the principal products, which products are further reacted under catalytic conditions to produce more highly chlorinated products and/or unsaturated products in liquid phase reactions in which numerous by-products containing more than 2 carbon atoms in the product stream of the thermal chlorination are detrimental to further processing in liquid phase catalytic hydrochlorination and/or dehydrochlorination reactions, the improvement which comprises chlorinating the thermal chlorination reactor effluent at a temperature below about 100° C. and in the absence of light and catalyst with up to about stoichiometric equivalent of chlorine, based on the concentration of said detrimental by-products in the thermal chlorination reactor effluent, and thereafter passing the entire chlorinated effluent stream without separation or purification to the liquid phase catalytic reaction, said chlorination rendering said detrimental by-products of the thermal chlorination harmless to the efficient operation of the subsequent process by preventing their deactivation of the catalyst.

2. The process of claim 1 wherein the low temperature chlorination is carried out at between about 0° C. and 100° C.

* * * * *